United States Patent
Wristers et al.

US 6,580,122 B1
Jun. 17, 2003

(54) TRANSISTOR DEVICE HAVING AN ENHANCED WIDTH DIMENSION AND A METHOD OF MAKING SAME

(75) Inventors: Derick J. Wristers, Bee Caves, TX (US); Jon D. Cheek, Round Rock, TX (US); John G. Pellerin, Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 0 days.

(21) Appl. No.: 09/812,521

(22) Filed: Mar. 20, 2001

(51) Int. Cl.[7] .......................... H01L 29/76; H01L 29/94; H01L 31/062; H01L 31/113; H01L 31/119; H01L 21/336; H01L 21/3205

(52) U.S. Cl. ..................... 257/330; 257/332; 257/374; 438/270; 438/259; 438/589

(58) Field of Search ................................. 257/283, 330, 257/332, 374; 438/270, 259, 589

(56) References Cited

U.S. PATENT DOCUMENTS 5,285,093 A * 2/1994 Lage et al.
6,017,801 A * 1/2000 Youn
6,133,105 A * 10/2000 Chen et al.
6,146,970 A * 11/2000 Witek et al.
6,159,801 A * 12/2000 Hsieh et al.
6,277,697 B1 * 8/2001 Lee
6,376,313 B1 * 4/2002 Goebel et al.

FOREIGN PATENT DOCUMENTS

JP     2001036048    * 7/1999

* cited by examiner

Primary Examiner—John F. Niebling
Assistant Examiner—Ron Pompey
(74) Attorney, Agent, or Firm—Williams, Morgan & Amerson

(57) ABSTRACT

The present invention is directed to a transistor having an enhanced width dimension and a method of making same. In one illustrative embodiment, the transistor comprises a semiconducting substrate, a recessed isolation structure formed in the substrate, the isolation structure defining a recess thereabove, a gate electrode and a gate insulation layer positioned above the substrate, a portion of the gate electrode and the gate insulation layer extending into the recess above the recessed isolation structure, and a source region and a drain region formed in the substrate. In another illustrative embodiment, the transistor comprises a semiconducting substrate, a recessed isolation structure that defines an active area having an upper surface and an exposed sidewall surface, a gate insulation layer and a gate electrode positioned above a portion of the upper surface and a portion of the exposed sidewall surface of the active area, and a source region and a drain region formed in the active area.

34 Claims, 5 Drawing Sheets

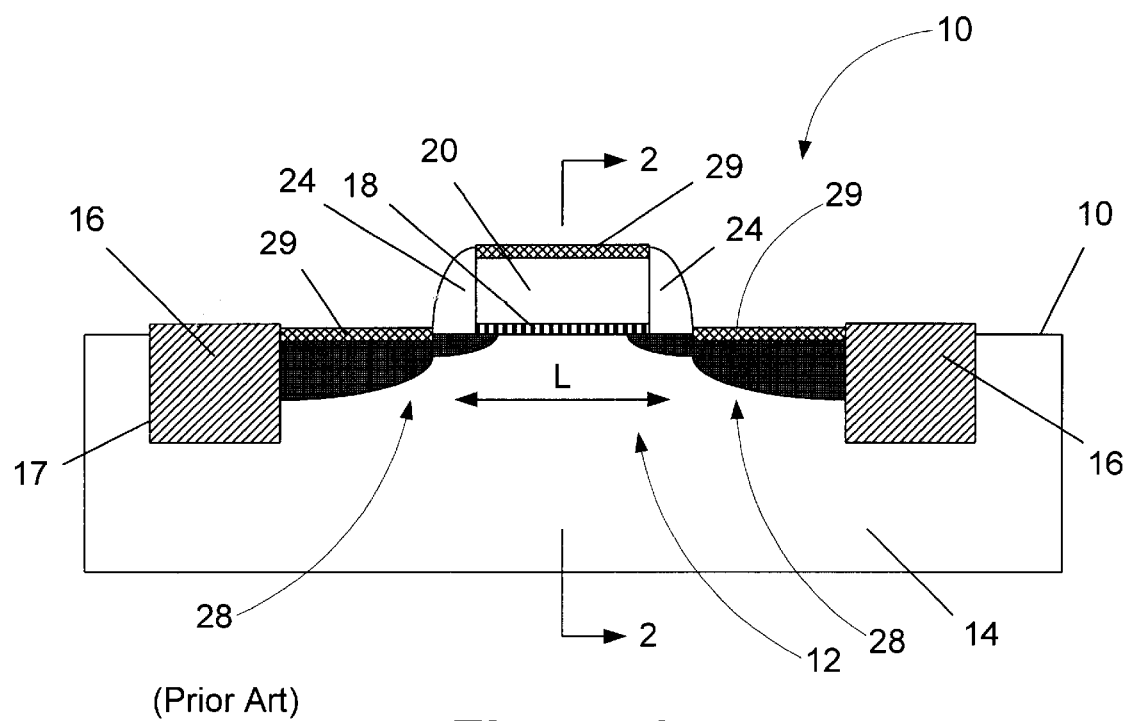
(Prior Art)  Figure 1
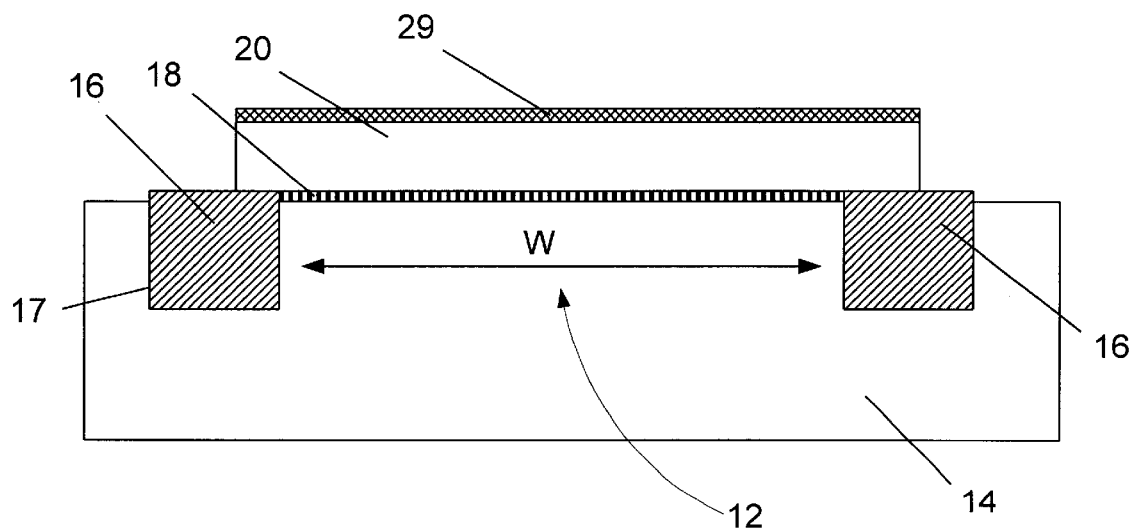
(Prior Art)  Figure 2

TRANSISTOR DEVICE HAVING AN ENHANCED WIDTH DIMENSION AND A METHOD OF MAKING SAME

BACKGROUND OF THE INVENTION

1. FIELD OF THE INVENTION

The present invention is generally directed to semiconductor devices and processing, and, more particularly, to a novel semiconductor device having an enhanced width dimension and a method of making same.

2. DESCRIPTION OF THE RELATED ART

There is a constant drive within the semiconductor industry to increase the operating speed of integrated circuit devices, e.g., microprocessors, memory devices, etc. This drive is fueled by consumer demands for computers and electronic devices that operate at increasingly greater speeds. This demand for increased speed has resulted in a continual reduction in the size of semiconductor devices, e.g., transistors. That is, the size of many components of a typical field effect transistor, e.g., channel length, source/drain junction depths, gate dielectric thickness, etc., are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

By way of background, FIG. 1 and FIG. 2 depict an illustrative transistor 10 for purposes of explaining one or more problems that may be solved or reduced by the present invention. FIG. 1 is a cross-sectional front view of the transistor 10 showing the channel length or transistor length "L." FIG. 2 is a cross-sectional side view of the transistor 10 shown in FIG. 1 taken along the line "2—2," i.e., showing the transistor width "W." As shown in FIG. 1, the transistor 10 is formed in an active area 12 that is defined in a semiconducting substrate 14 by an isolation structure 16 formed therein. The transistor 10 is comprised of a gate insulation layer 18, a gate electrode 20, a sidewall spacer 24, and a plurality of source/drain regions 28. The transistor 10 is also comprised of metal silicide layers 29 formed above the source/drain regions 28 and the gate electrode 20.

All of the various components of the transistor 10 depicted in FIG. 1 may be formed using a variety of known processing techniques, and they may be comprised of a variety of materials. For example, the gate insulation layer 18 may be comprised of a thermally grown layer of silicon dioxide, the gate electrode 20 may be comprised of polysilicon, the sidewall spacer 24 may be comprised of silicon dioxide, and the metal silicide regions 29 may be comprised of, for example, cobalt silicide or titanium silicide. The isolation structure 16 is typically comprised of an insulating material, such as silicon dioxide, or other like material. The isolation structure 16 may be constructed by forming a trench 17 in the substrate 14, filling the trench with an appropriate insulating material, e.g., silicon dioxide, and, thereafter, performing a chemical mechanical polishing operation to remove any excess material.

In designing modern integrated circuit devices, one parameter of a transistor that is of particular importance is known as its drive current. Stated simply, the drive current of a transistor is the amount of current flowing from the drain region to the source region of a transistor. All other things being equal, it is desirable that transistors have as large a drive current as possible without otherwise adversely impacting the performance of the transistor, i.e., without generating excessive heat or excessive off-state leakage currents, etc.

The drive current of the device may be increased by reducing the channel length of the transistor. However, all other things being equal, the smaller the channel length of the transistor, the greater the off-state leakage current. Moreover, the off-state leakage current increases exponentially as the channel length of the device decreases. Off-state leakage currents also increase as the transistor width increases, but at a rate that is less than the exponential rate associated with reductions in the channel length of a device. Thus, in attempting to increase the drive current of a transistor, increasing the width of the transistor results in lower off-state leakage currents, as compared to increasing the drive current the same amount by reducing the channel length. Moreover, to a great extent, reducing the channel length of the device is limited by available photolithography and etching processes.

Typically, the amount of drive current that can be generated per unit width ("w") of the transistor is a known value. Thus, when a total drive current is desired or required for a particular circuit application, the required width of the transistor to accomplish this purpose may be readily determined. Thus, for a given type of transistor, an application requiring a transistor having a width of 30 w may be satisfied by a single transistor having a width of approximately 30 w or six transistors, arranged in parallel, each having a width of approximately 5 w. Using this process, the layout of integrated circuit devices across the surface of a portion of a semiconducting substrate is accomplished, with the ultimate goal being to minimize consumption of wafer plot space, i.e., to maximize the use of available substrate. Thus, it would be desirable to have a transistor in which the width dimension of a substrate can be maximized in a given plot space of semiconducting substrate.

The present invention is directed to a method that solves or reduces some or all of the aforementioned problems.

SUMMARY OF THE INVENTION

The present invention is directed to a transistor having an enhanced width dimension and a method of making same. In one illustrative embodiment, the transistor comprises a semiconducting substrate, a recessed isolation structure formed in the substrate, the isolation structure defining a recess thereabove, a gate electrode and a gate insulation layer positioned above the substrate, a portion of the gate electrode and the gate insulation layer extending into the recess above the recessed isolation structure, and a source region and a drain region formed in the substrate. In another illustrative embodiment, the transistor comprises a semiconducting substrate, a recessed isolation structure that defines an active area having an upper surface and an exposed sidewall surface, a gate insulation layer and a gate electrode positioned above a portion of the upper surface and a portion of the exposed sidewall surface of the active area, and a source region and a drain region formed in the active area.

In one illustrative embodiment, the method of making a transistor comprises providing a semiconducting substrate, forming a recessed isolation structure in a trench formed in the substrate, the recessed isolation structure thereby defining a recess in the substrate, forming a gate insulation layer and a gate electrode above the substrate, a portion of the gate insulation layer and gate electrode extending into the recess in the substrate and above the recessed isolation structure, and forming a plurality of source/drain regions in the substrate adjacent the gate electrode.

BRIEF DESCRIPTION OF THE DRAWINGS

The invention may be understood by reference to the following description taken in conjunction with the accompanying drawings, in which like reference numerals identify like elements, and in which:

FIG. 1 is a cross-sectional front view of an illustrative prior art transistor in the transistor length direction;

FIG. 2 is a cross-sectional side view of the prior art transistor shown in FIG. 1 along the line "2—2";

Figure 3:
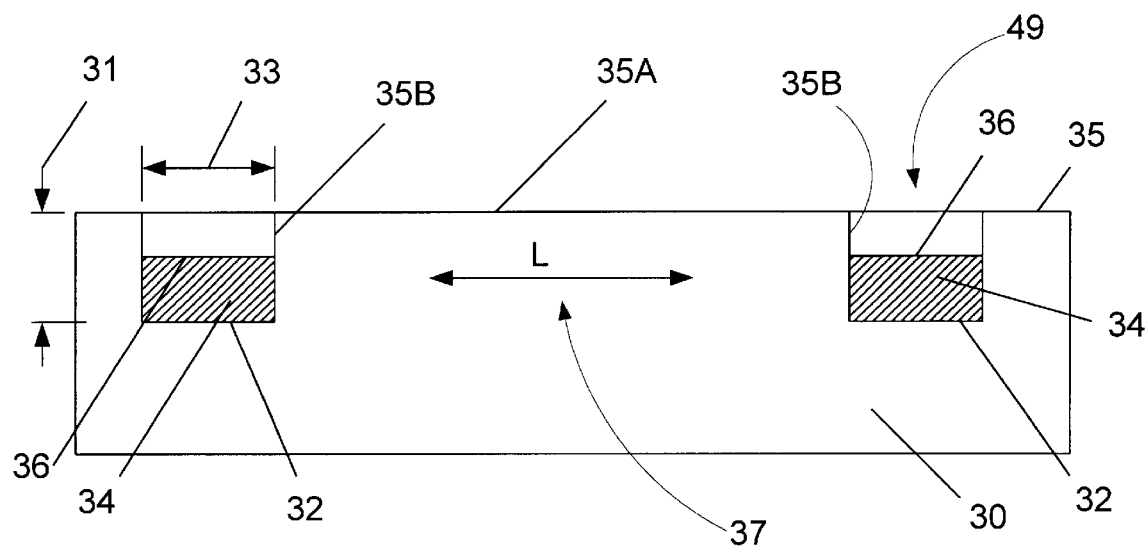
FIG. 3 is a cross-sectional front view of a partially formed transistor in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features depicted in the drawings may be exaggerated or reduced as compared to the size of those features or regions on fabricated devices. Nevertheless, the attached drawings are included to describe and explain illustrative examples of the present invention. As will be readily apparent to those skilled in the art upon a complete reading of the present application, the present method is applicable to a variety of technologies, e.g., NMOS, PMOS, CMOS, etc., is readily applicable to a variety of devices, including, but not limited to, logic devices, memory devices, etc.

In general, the present invention is directed to a transistor device having an enhanced width dimension and a method of making same. As will re recognized after a complete reading of the present application, the present invention provides a method to maximize the width of a transistor in a given plot space of semiconducting substrate. In turn, integrated circuit devices incorporating such transistors may be more efficient in terms of plot spacer consumption.

As shown in FIG. 3, a trench 32 is formed in a semiconducting substrate 30. For reference, the transistor length direction "L" is also shown in FIG. 1. A recessed isolation material 34, comprised of materials such as silicon dioxide, silicon oxynitride, etc., is formed in the trench 32. The width 33 and the depth 31 of the trench 32 may be varied as a matter of design choice. In one embodiment, the depth 31 of the trench 32 ranges from approximately 3000–6000 Å. The width 33 of the trench 32 may vary from a minimum of the smallest feature size that can be patterned using existing photolithography and etching techniques, up to any desired width. In one illustrative embodiment, the width 33 of the trench 32 ranges from approximately 2000–3000 Å.

The recessed isolation material 34 may be formed in the trench 32 by a variety of techniques. In one illustrative embodiment, a layer of insulating material (not shown) is blanket deposited above the surface 35 of the substrate 30 and in the trench 32. Thereafter, a chemical mechanical polishing operation is performed on the layer of insulating material such that the insulating material in the trench 32 is approximately planar (not shown) with the surface 35 of the substrate 30. An etching process, such as a wet etching process, may then be performed to reduce the level of insulating material 34 in the trench 32 to the level depicted in FIG. 3. In one illustrative embodiment, the insulating material 34 is removed until such time as a surface 36 of the isolation material 34 in the trench 32 is positioned approximately 1000–1500 Å beneath the surface 35 of the substrate 30. This process results in the definition of an active island 37 of substrate material having an exposed upper surface 35A and an exposed sidewall surface 35B. The island 37 of substrate material may be of any desired shape, i.e., circular, oval, rectangular, etc. This process also results in the definition of a recess 49 in the substrate 30 above the recessed isolation material 34. In the disclosed embodiment, the recess 49 has a depth of approximately 1000–1500 Å.

Thereafter, one or more channel doping operations are performed at this stage of manufacturing. For example, in one illustrative embodiment, a threshold voltage implant process is performed on the device. This may be accomplished by performing a four-way angled channel implant process wherein each of the angled implants are spaced approximately 90 degrees apart with respect to one another. In one illustrative embodiment, this threshold voltage implant may be accomplished by a four-way angled implant process performed at an implant angle of approximately 30–50 degrees (with respect to a line perpendicular to the surface 35 of the substrate 30) using dopant atoms at a concentration ranging from approximately $1–3\times10^{12}$ ions/cm$^2$ per rotation. For an NMOS device, boron may be implanted during the threshold voltage implant step at an energy level ranging from approximately 10–15 keV. For a PMOS device, such a threshold voltage implant may be performed using phosphorous at an energy level ranging from approximately 90–110 keV. Additional channel doping implantation processes may be performed at this time if desired or required by the device under construction.

Figure 4:
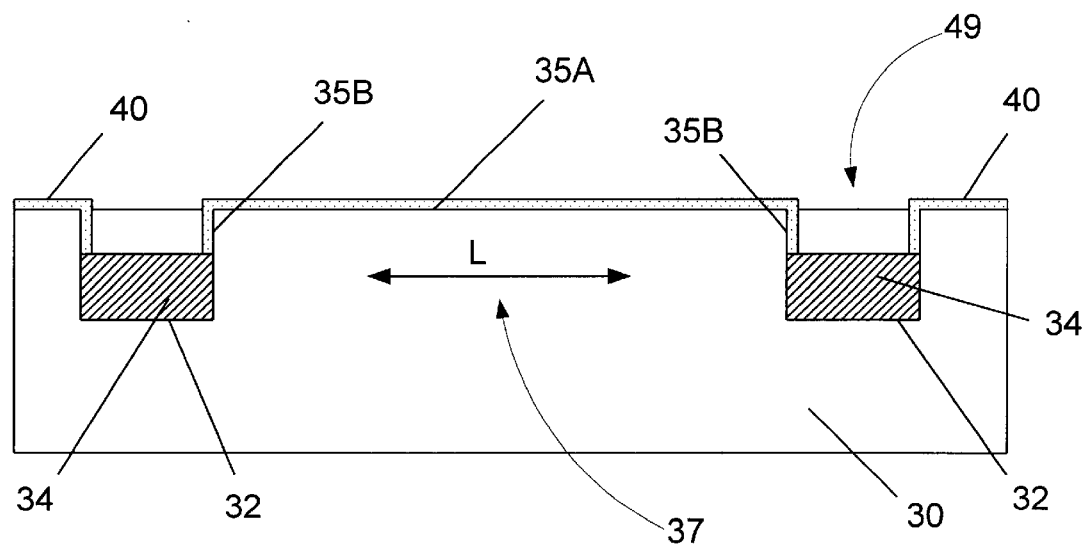
FIG. 4 is a cross-sectional front view of the device shown in FIG. 3 after a gate insulation layer has been formed thereabove.

Thereafter, as shown in FIG. 4, a gate insulation layer 40 for the transistor 10 is formed for the device. The gate insulation layer 40 may be formed from a variety of materials, such as silicon dioxide, silicon oxynitride, silicon nitride, or any dielectric material having a dielectric constant less than approximately four. The gate insulation layer 40 may be formed by a variety of processes, e.g., chemical vapor deposition (CVD), thermal growth, etc. In one illustrative embodiment, as shown in FIG. 4, the gate insulation layer 40 is comprised of a thermally grown layer of silicon dioxide having a thickness ranging from approximately 20–50 Å.

Figure 5:
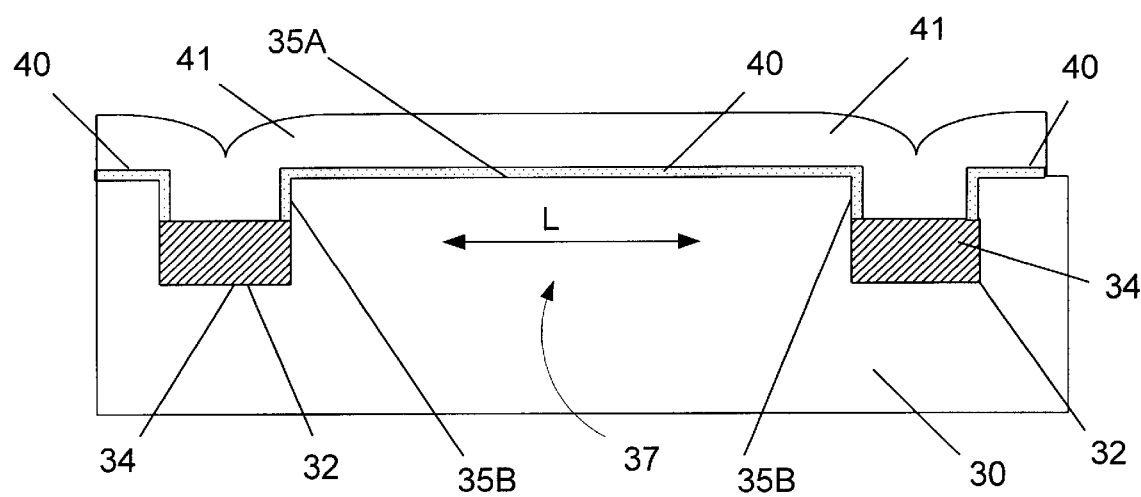
FIG. 5 is a cross-sectional front view of the device shown in FIG. 4 after a layer of polysilicon has been formed thereabove.

Next, as shown in FIG. 5, a layer of polysilicon 41 is blanket deposited above the gate insulation layer 40 and above the recessed isolation material 34. The layer of polysilicon 41 may be formed by a variety of techniques, e.g., chemical vapor deposition, low pressure chemical vapor deposition, etc. In one illustrative embodiment, the layer of polysilicon 41 has a thickness ranging from approximately 1000–2000 Å, and it is formed by conformally depositing the layer of polysilicon 41 using a chemical vapor deposition process.

Figure 6A:
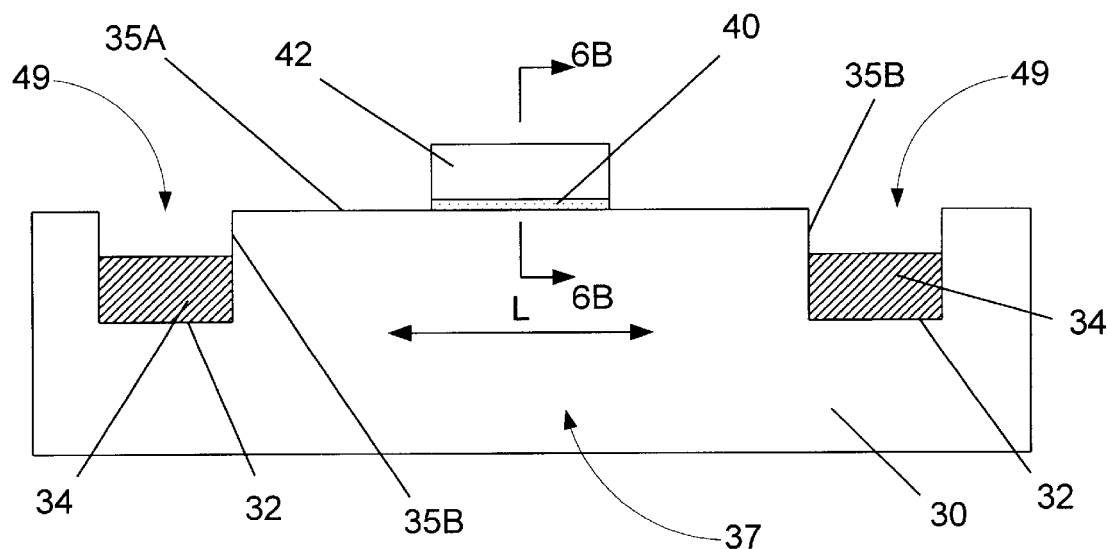
FIG. 6A is a cross-sectional front view of the device shown in FIG. 5 after a gate electrode has been patterned from the layer of polysilicon.
Figure 6B:
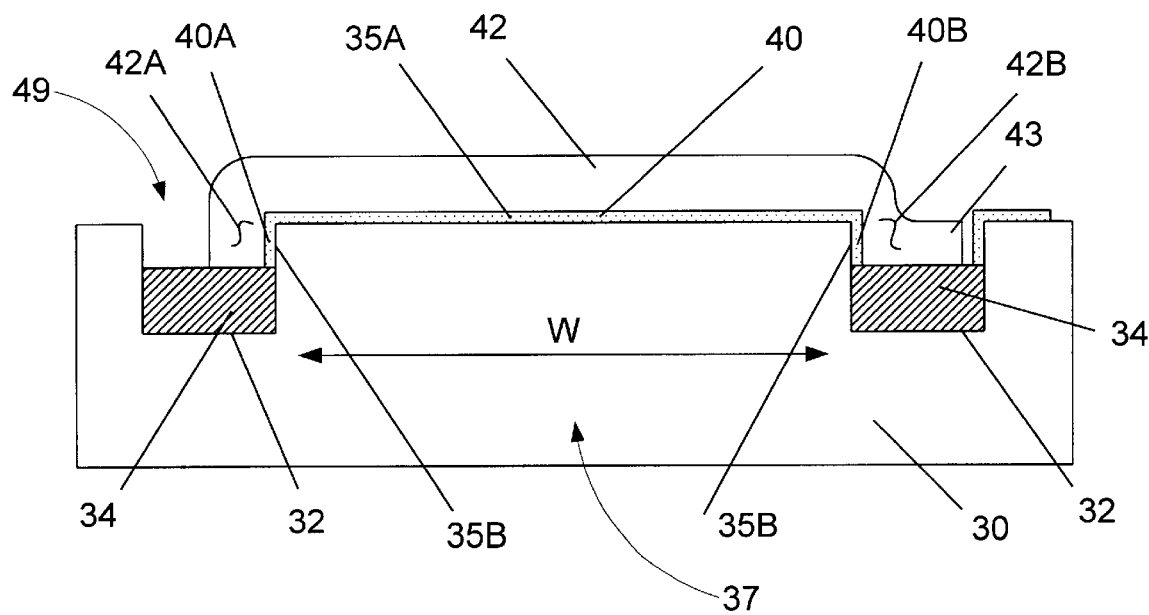
FIG. 6B is a cross-sectional side view, in the transistor width direction, of the device shown in FIG. 6A taken along the line "6B—6B"

Next, as shown in FIG. 6A, using traditional photolithography and one or more etching processes, a gate electrode 42 is patterned from the layer of polysilicon 41. The gate insulation layer 40 may also be patterned at this time, as shown in FIG. 6A. FIG. 6B is a side view of the structure depicted in FIG. 6A taken along the line "6B—6B." That is, FIG. 6B is a cross-sectional view of the device in the transistor width dimension "W." As shown therein, a portion 43 of the gate electrode 42 extends beyond the isolation structure 34. The portion 43 of the gate electrode 42 is coupled to a power supply (not shown) so that a voltage may be applied to the gate electrode 42.

Then, halo implant regions (not shown) are formed in the device by performing a four-way angled halo implant process. Each of the angled implant processes are performed at an angle ranging from approximately 30–45 degrees with respect to a line generally perpendicular to the surface 35 of the substrate 30, and at a concentration level ranging from approximately $1–6\times10^{13}$ ions/cm$^2$ total (for all four rotations). In an illustrative NMOS device, boron atoms may be implanted at an energy level ranging from approximately 7–15 keV. In an illustrative PMOS device, arsenic may be implanted during this halo implant process at an energy level ranging from approximately 40–65 keV.

Figure 7C:
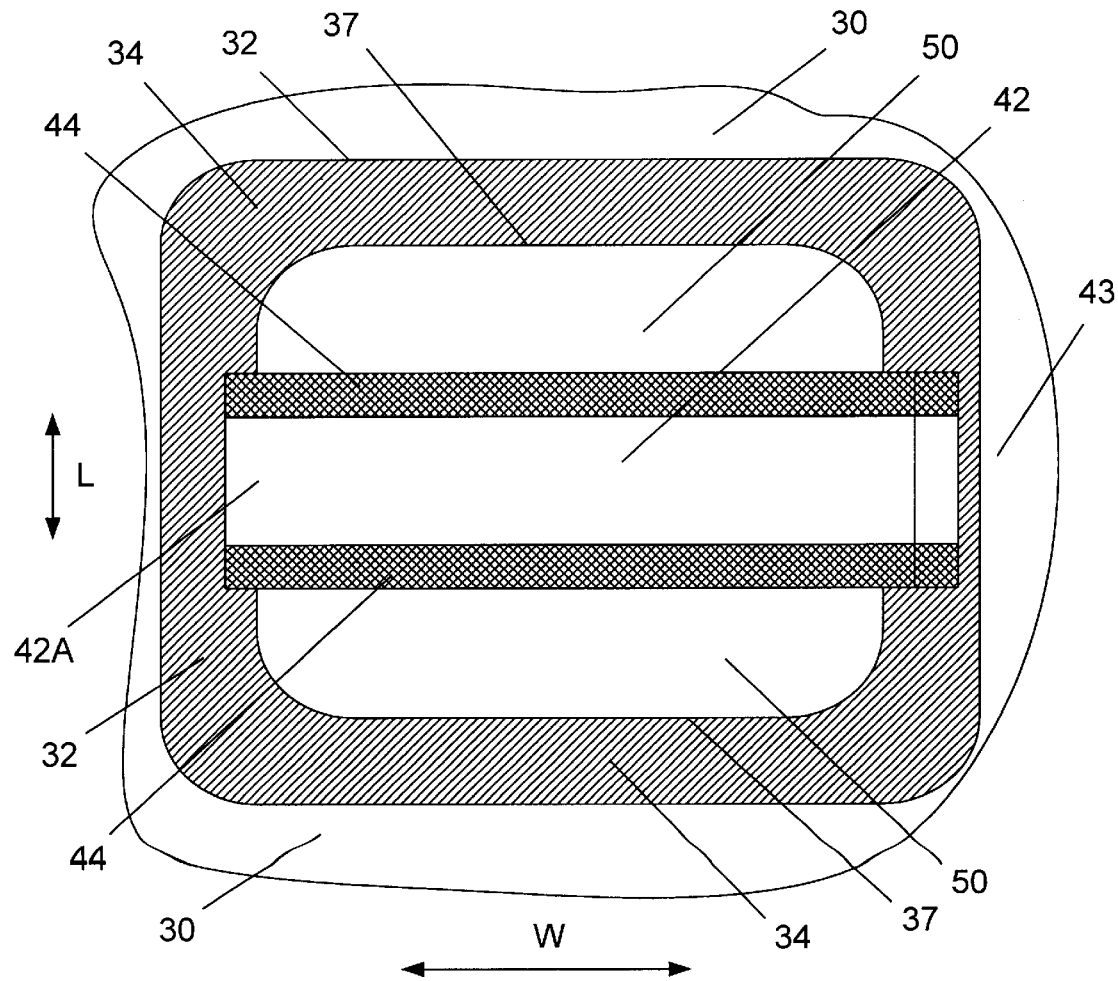
FIG. 7C is a plan view of the device shown in FIG. 7A.
Figure 7A:
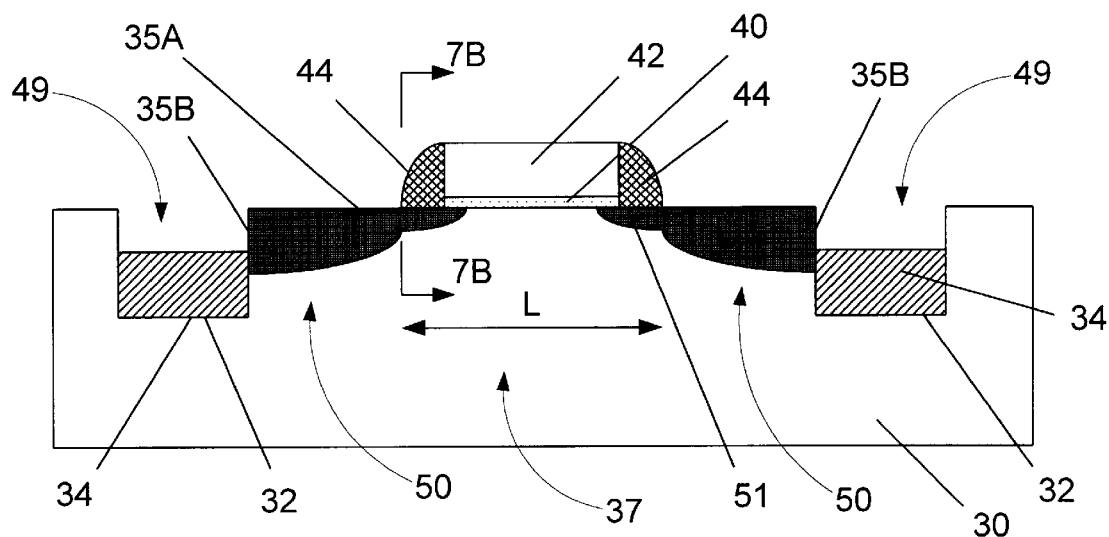
FIG. 7A is a cross-sectional front view of the device shown in FIG. 6A after source/drain regions have been formed on the device.
Figure 7B:
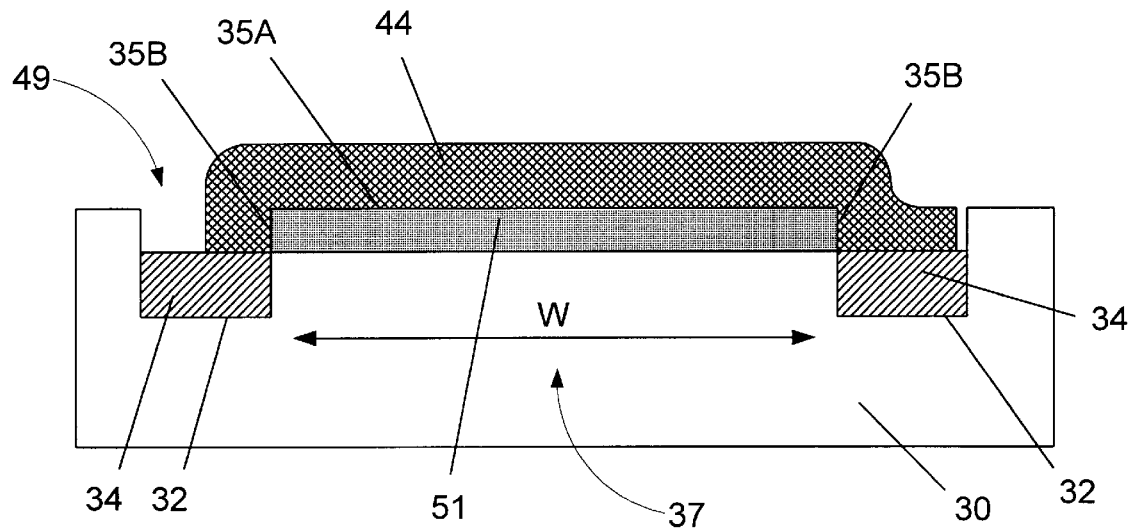
FIG. 7B is a cross-sectional side view, in the transistor width direction, of the device shown in FIG. 7A taken along the line "7B—7B"

Thereafter, source and drain regions 50 for the device may be formed using a variety of process flows. FIGS. 7A and 7B (side view taken along the line "7B–7B" in FIG. 7A) depict the transistor after the source/drain regions 50 have been formed. FIG. 7C is a plan view of the device shown in FIG. 7A. In one illustrative embodiment, a source/drain extension implant process is performed to form source/drain extensions 51 of the completed device. This extension implantation process may be performed at a relatively low energy level and at a relatively high concentration of dopant atoms.

For example, the concentration of dopant atoms in the extension implant process may vary from approximately $1\times10^{14}$ to $2\times10^{15}$ ions/cm$^2$ of the appropriate dopant atoms, e.g., arsenic (Ar) or phosphorous (P) for NMOS technology, boron (B) or boron difluoride (BF$_2$) for PMOS technology, etc. The energy level for the extension implant process will vary depending upon the dopant material used in the process. For example, in one illustrative embodiment for forming the source/drain extension implants in an NMOS device, the extension implantation process is performed using arsenic as the dopant atoms at a concentration ranging from approximately $6\times10^{14}$ to $2\times10^{15}$ ions/cm$^2$ and at an energy level ranging from approximately 3–15 keV. Typically, the extension implant process will result in implant regions in the substrate that are generally self-aligned with respect to the gate electrode 42 (as implanted). However, for a PMOS device, a small sidewall spacer (not shown) may be formed adjacent the gate electrode 42 prior to performing the extension implant step. This spacer is used in PMOS devices due to the increased mobility of the dopant atoms that may be implanted, e.g., boron.

Next, as indicated in FIGS. 7A–7C, a sidewall spacer 44 is formed adjacent the gate electrode 42. The sidewall spacer 44 is formed by depositing a layer (not shown) of spacer material above the surface of the device and thereafter performing an anisotropic etching process to define the spacer 44. The layer of spacer material may be comprised of a variety of materials, such as silicon dioxide, silicon oxynitride, or other like materials. Moreover, it may be formed by any of a variety of techniques for forming such layers, such as chemical vapor deposition (CVD), physical vapor deposition (PVD), etc.

Next, a source/drain implant process is performed on the device. Note that the source/drain implant process is self-aligned with respect to the sidewall spacer 44. The dopant concentration levels and implant energy for the source/drain implant process may vary. For example, the concentration of dopant atoms in the source/drain implantation process may vary from approximately $5\times10^{14}$ to $5\times10^{15}$ ions/cm$^2$ of the appropriate dopant atoms, e.g., arsenic or phosphorous for NMOS technology, boron for PMOS technology, etc. The energy level for the source/drain implantation process will vary depending upon the dopant material. For example, in one illustrative embodiment for forming the source/drain regions in an NMOS device, the source/drain implantation process is performed using arsenic as the dopant atoms at a concentration of approximately $5\times10^{14}$ to $5\times10^{15}$ ions/cm$^2$ and at an energy level ranging from approximately 20–70 keV.

Thereafter, one or more thermal anneal processes is performed to activate the dopant atoms introduced into the substrate 30 during various ion implant processes described above, and to repair the damage to the lattice structure of the semiconducting substrate 30 resulting from the ion implantation processes. In one embodiment, this anneal process may be at a temperature ranging from approximately 1000–1050° C. for a duration of approximately 5–20 seconds in a rapid thermal anneal chamber. Note that during this process, the previously implanted dopant atoms migrate, or move, from their original implanted position. This migration of the dopant atoms is generally isotropic in direction.

As shown in FIGS. 6A, 6B and 7A–7C, the present invention is directed to a novel transistor structure. The gate electrode 42 has first and second ends 42A, 42B, respectively. The first and second ends 42A, 42B, as well as first and second portions 40A, 4B of the gate insulation layer 40 thereunder, are positioned above a portion of the exposed sidewall 35B of the active area 37. The remainder of the gate electrode 42 is positioned above the surface 35A of the active area 37. In the embodiment depicted in the attached drawings, the first end 42A of the gate electrode 42 is shown as being patterned such that it does not extend beyond the recessed isolation structure 34. Of course, if desired, the first end 42A of the gate electrode 42 may be patterned so as to extend completely beyond the recessed isolation structure 34 in a manner similar to the configuration depicted for the portion 43 of the gate electrode 42 depicted in FIGS. 6B and 7B. Stated another way, the novel transistor structure disclosed herein is comprised of a gate electrode 42 and a gate insulation layer 40 wherein a portion of the gate electrode 42 and the gate insulation layer 40 extends downwardly into a recess 49 in the substrate above a recessed isolation structure 34. In the disclosed embodiment, both ends 42A, 42B of the gate electrode 42 and both portions 40A, 40B of the gate insulation layer 40 extend into the recess 49 above the recessed isolation structure 34.

After the formation of the gate electrode 42, additional insulating material (not shown), e.g., silicon dioxide, BPSG, etc., may be blanket deposited above the device shown in FIGS. 7A and 7B to fill the portions of the recess 49 not filled, or at least partially filled by the downwardly extending portions of the gate electrode 41 and gate insulation layer 40.

The present invention is directed to a transistor having an enhanced width dimension and a method of making same. In one illustrative embodiment, the transistor comprises a semiconducting substrate 30, a recessed isolation structure 34 formed in the substrate 30, the isolation structure 34 defining a recess 49 thereabove, a gate electrode 42 and a gate insulation layer 40 positioned above the substrate 30, a portion of the gate electrode 42 and the gate insulation layer 40 extending into the recess 49 above the recessed isolation structure 49, and a source region 51A and a drain region 51B formed in the substrate 30. In another illustrative embodiment, the transistor comprises a semiconducting substrate 30, a recessed isolation structure 34 that defines an active area 37 having an upper surface 35A and an exposed sidewall surface 35, a gate insulation layer 40 and a gate electrode 42 positioned above a portion of the upper surface 35A and a portion of the exposed sidewall surface 35B of the active area 37, and a source region 51A and a drain region 51B formed in the active area 37.

In one illustrative embodiment, the method of making a transistor comprises providing a semiconducting substrate 30, forming a recessed isolation structure 34 in a trench 32 formed in the substrate 30, the recessed isolation structure 34 thereby defining a recess 49 in the substrate 30, forming a gate insulation layer 40 and a gate electrode 42 above the substrate 30, a portion of the gate insulation layer 40 and gate electrode 42 extending into the recess 49 above the recessed isolation structure 49, and forming a plurality of source/drain regions 51A, 51B in the substrate 30 adjacent the gate electrode.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A transistor, comprising:
   a semiconducting substrate;
   a recessed isolation structure formed in said substrate, said isolation structure defining a recess thereabove;
   a gate electrode and a gate insulation layer formed above said substrate, a portion of said gate electrode and said gate insulation layer extending into said recess above said recessed isolation structure; and
   a source region and a drain region formed in said substrate.

2. The transistor of claim 1, wherein said semiconducting substrate is comprised of silicon.

3. The transistor of claim 1, wherein said recessed isolation structure is comprised of at least one of silicon dioxide and silicon oxynitride.

4. The transistor of claim 1, wherein said recessed isolation structure has a surface that is positioned approximately 1000–1500 Å below a surface of said substrate.

5. The transistor of claim 1, wherein said recessed isolation structure is formed in a trench having a width ranging from approximately 2000–3000 Å and a depth ranging from approximately 4000–5000 Å.

6. The transistor of claim 1, wherein said gate electrode is comprised of polysilicon.

7. The transistor of claim 1, wherein said gate insulation layer is comprised of at least one of silicon dioxide and silicon oxynitride.

8. The transistor of claim 1, wherein said gate electrode has a thickness ranging from approximately 1000–2000 Å.

9. The transistor of claim 1, wherein said gate insulation layer has a thickness ranging from approximately 20–50 Å.

10. The transistor of claim 1, wherein said source region and said drain region are each comprised of an extension implant region and a source/drain implant region.

11. The transistor of claim 1, wherein said gate electrode has first and second end portions that extend into said recess.

12. The transistor of claim 11, wherein said first and second end portions extending into said recess are positioned above a portion of a sidewall of an active region of said substrate defined by said recessed isolation structure.

13. A transistor, comprising:
   a semiconducting substrate comprised of silicon;
   a recessed isolation structure formed in said substrate, said isolation structure defining a recess thereabove;
   a gate electrode comprised of polysilicon and a gate insulation layer formed above said substrate, a portion of said gate electrode and said gate insulation layer extending into said recess above said recessed isolation structure; and
   a source region and a drain region formed in said substrate.

14. The transistor of claim 13, wherein said recessed isolation structure is comprised of at least one of silicon dioxide and silicon oxynitride.

15. The transistor of claim 13, wherein said recessed isolation structure has a surface that is positioned approximately 1000–1500 Å below a surface of said substrate.

16. The transistor of claim 13, wherein said recessed isolation structure is formed in a trench having a width ranging from approximately 2000–3000 Å and a depth ranging from approximately 4000–5000 Å.

17. The transistor of claim 13, wherein said gate insulation layer is comprised of at least one of silicon dioxide and silicon oxynitride.

18. The transistor of claim 13, wherein said gate electrode has a thickness ranging from approximately 1000–2000 Å.

19. The transistor of claim 13, wherein said gate insulation layer has a thickness ranging from approximately 20–50 Å.

20. The transistor of claim 13, wherein said source region and said drain region are each comprised of an extension implant region and a source/drain implant region.

21. The transistor of claim 13, wherein said gate electrode has first and second end portions that extend into said recess in said substrate.

22. The transistor of claim 21, wherein said first and second end portions extending into said recess in said substrate are positioned above a portion of a sidewall of an active region of said substrate defined by said recessed isolation structure.

23. A transistor, comprising:
- a semiconducting substrate;
- a recessed isolation structure defining an active area having an upper surface and an exposed sidewall surface;
- a gate insulation layer and a gate electrode positioned above a portion of said upper surface and a portion of said exposed sidewall surface of said active area; and
- a source region and a drain region formed in said active area.

24. The transistor of claim 23, wherein said semiconducting substrate is comprised of silicon.

25. The transistor of claim 23, wherein said recessed isolation structure is comprised of at least one of silicon dioxide and silicon oxynitride.

26. The transistor of claim 23, wherein said recessed isolation structure has a surface that is positioned approximately 1000–1500 Å below a surface of said substrate.

27. The transistor of claim 23, wherein said recessed isolation structure is formed in a trench having a width ranging from approximately 2000–3000 Å and a depth ranging from approximately 4000–5000 Å.

28. The transistor of claim 23, wherein said gate electrode is comprised of polysilicon.

29. The transistor of claim 23, wherein said gate insulation layer is comprised of at least one of silicon dioxide and silicon oxynitride.

30. The transistor of claim 23, wherein said gate electrode has a thickness ranging from approximately 1000–2000 Å.

31. The transistor of claim 23, wherein said gate insulation layer has a thickness ranging from approximately 20–50 Å.

32. The transistor of claim 23, wherein said source region and said drain region are each comprised of an extension implant region and a source/drain implant region.

33. The transistor of claim 23, wherein said gate electrode has first and second end portions that extend into a recess in said substrate defined by said recessed isolation structure.

34. The transistor of claim 33, wherein said first and second end portions extending into said recess in said substrate are positioned above a portion of a sidewall of an active region of said substrate defined by said recessed isolation structure.

* * * * *